United States Patent [19]

Vandenbergh et al.

[11] Patent Number: 5,648,466
[45] Date of Patent: Jul. 15, 1997

[54] METHOD FOR DETECTING BOVINE DIARRHOEA VIRUS INFECTION, NUCLEOTIDE SEQUENCE ENCODING A PROTEIN INDUCED BY THIS VIRUS INFECTION AND RECOMBINANT PROTEINS AND ANTIGENS RELATING THERETO

[75] Inventors: Danielle Marie Helene Jeanne Vandenbergh, Cheratte; Corine Martine Therese Ghislaine LeComte, Ocquier, both of Belgium; Gilles-Emile Chappuis, Lyons; Jean-Jacques Pin, Saint Bonnet de Mure, both of France

[73] Assignee: Rhone Merieux, Lyons, France

[21] Appl. No.: 467,923

[22] Filed: Jun. 6, 1995

Related U.S. Application Data

[62] Division of Ser. No. 417,276, Apr. 5, 1995, which is a continuation of Ser. No. 895,999, Jun. 11, 1992, abandoned.

[30] Foreign Application Priority Data

Nov. 6, 1991 [FR] France ................................ 91 07076

[51] Int. Cl.⁶ ........................... C07H 21/04; C07K 14/00
[52] U.S. Cl. .............................................. 530/350; 536/23.7
[58] Field of Search ............................... 536/23.72, 24.2; 530/350

[56] References Cited

PUBLICATIONS

Collett et al, Virology 165:191–199 (1988).
Collett, et al, Virology 165:200–208 (1988).
Kwang et al, Biochem. Biophy. Res. Comm 178:1326–1334 (1991).
Murhammer, App. Biochem. Biotech. 31:283–292 (1991).

Primary Examiner—Eggerton A. Campbell
Attorney, Agent, or Firm—Larson and Taylor

[57] ABSTRACT

The invention is directed to a method of detecting infection of a blood sample by various strains of bovine diarrhoea virus (BVD) including a first test wherein anti-bovine diarrhoea virus antibodies are detected by means of a recombinant antigen comprising the BVD p80 protein expressed by a eukaryotic host and a second test wherein viral particles are detected by means of antibodies directed against the BVD p80 viral protein. The method is particularly useful in detecting pathogenic conditions such as persistent viremias and acute infections caused by BVD viruses, and is particularly advantageous because it is an extremely sensitive and efficient test and because it is capable of detecting infections caused by any one of a wide variety of BVD strains. The recombinant antigen employed in the method is preferably encoded by the nucleotide sequence listed as SEQ ID No: 1.

5 Claims, 3 Drawing Sheets

METHOD FOR DETECTING BOVINE DIARRHOEA VIRUS INFECTION, NUCLEOTIDE SEQUENCE ENCODING A PROTEIN INDUCED BY THIS VIRUS INFECTION AND RECOMBINANT PROTEINS AND ANTIGENS RELATING THERETO

This is a division of application Ser. No. 08/417,276 filed Apr. 5, 1995, which is a continuation of application Ser. No. 07/895,999, filed Jun. 11, 1992, now abandoned.

The present invention relates to a method for detecting bovine diarrhoea virus infection, a nucleotide sequence encoding a protein associated with this virus infection and recombinant proteins and antigens relating thereto.

Bovine diarrhoea virus (BVD) is an infectious single-stranded RNA-containing enveloped virus which is related to the conventional hog cholera virus and to the Border disease virus, the three viruses forming the Pestivirus genus which belongs to the Togaviridae family. The BVD virus is universally distributed in bovine populations and manifests itself by a wide range of clinical symptoms associated with congenital, respiratory or enteric diseases (bovine viral diarrhoea, mucosal disease).

Isolates of BVD viruses may be classified into two distinct categories or biotypes according to their effects during cell culture: cytopathogenic and noncytopathogenic.

Acute infection of seronegative animals is normally benign or subclinical. On the other hand, intrauterine infection of the foetus, during approximately the first four months after the start of pregnancy, by a noncytopathogenic strain can not only produce abortions, still births or the birth of weak calves, but also the birth of calves having persistent viremia, that is to say permanently excreting the virus. This period of four months corresponds to an absence of immunity in the foetus. When the immune system then becomes competent, it recognises the virus as its own and a situation of immunotolerance is established (absence of antibodies). These animals will not be able to survive a subsequent infection by a cytopathogenic strain of homologous BVD virus.

Maintenance of the noncytopathogenic virus within the bovine population is ensured by its slow dissemination following acute infection of seronegative animals and, in particular, by its continual excretion by animals having persistent viremia. (See J. Brownlie et al., Ann. Rech. Vet. (1987) 18:157–166).

A. Fenton et al. (Journal of Virological Methods, 27 (1990), 253–260) detect the Pestivirus antigens in the blood of viremic sheep infected in a persistent manner by the Border disease virus, by an ELISA carried out so as to detect a specific antigen in the leucocytes of these animals. This technique requires prior purification of the leucocytes, which proves to be long and complex to carry out.

The genome of the Osloss viral strain, of cytopathogenic biotype, has been cloned and completely sequenced by Renard et al. (Patent Application EP-A-0,208,672 of 8 Jul. 1985). The Applicant has found that the open reading frame (ORF) of the BVD Osloss genomic sequence, which is 12408 nucleotides in length, has a coding capacity of 3951 amino acids (aas).

In an abstract distributed during the symposium on ruminant infections by Pestiviruses which was held at Hanover on 8 and 9 Jun. 1990, C. Lecomte et al. indicate the identification of a cDNA translational product of the BVD virus immunoprecipitated by monoclonal antibodies recognising the nonstructural protein p80 of a certain number of Pestivirus strains. The same cDNA is expressed in *E. coli* and the antigen produced is used in competition ELISA to detect anti-BVD antibodies in the bovine serum.

The preparation and the characterisation of a series of monoclonal antibodies have been described by C. Lecomte et al. (Veterinary Microbiology, 23 (1990), 193–201), as well as the use of a fusion protein produced in *E. coli* as recombinant antigen enabling anti-BVD serum antibodies to be detected in a competition ELISA with the chosen monoclonal antibodies.

In an abstract distributed at the VIIIth International Congress of Virology which was held in Berlin on 26 to 31 Aug. 1990, C. Lecomte et al. proposed the use of two ELISA tests for the detection on the one hand of anti-BVD antibodies and, on the other hand, of viral antigens. The anti-BVD antibodies in the serum would be detected by a competition ELISA using a BVD Osloss recombinant antigen p80 produced in *E. coli* and monoclonal antibodies specifically directed against the p80 protein of a certain number of Pestivirus strains. The second ELISA would be a sandwich type ELISA using two monoclonal antibodies and which would permit the detection of antigens in persistent veremic animals.

However, the Applicant has found that the p80 protein produced in *E. coli* is not recognised by all the anti-p80 monoclonal antibodies and especially by some of those exhibiting polyspecificity, that is to say reacting towards several or all Pestivirus strains, which undermines the chances of being able to detect in a single operation any infection by any BVD strain, all the more so as the second ELISA, based on the use of two monoclonal antibodies, could also not be sufficiently polyspecific.

The objective of the invention is to provide a very sensitive method of detection permitting a complete and effective control of infection which may be caused in livestock by a BVD virus of any type, and relating to both the detection of persistent viremias and acute infections.

The subject of the invention is therefore a method for detecting infection of a blood sample by the BVD virus, comprising a first test for the detection of anti-BVD antibodies and a second test for the detection of viral particles, characterised in that the anti-p80 antibodies are detected by means of a recombinant antigen comprising the BVD virus nonstructural protein p80, produced in a eukaryotic host, and preferably an anti-p80 monoclonal antibody used as competing antibody, and in that the presence of viral particles is detected by means of polyclonal or monoclonal antibodies directed against the BVD virus protein p80, and preferably of a serum directed against the recombinant p80 antigen produced in a eukaryotic or prokaryotic host, for the detection of persistent viremias and acute infections by any BVD strain.

The p80 protein is preferably derived from BVD Osloss and the nucleotide sequence encoding this protein has been completely sequenced. The sequence is given in the list of attached sequences, under the reference SEQ ID No: 1. The Applicant has thus advantageously located one potential cleavage site of p80 (KVR: lysine-valine-arginine) corresponding to the end of p80.

The p80 protein is expressed in viral or eukaryotic vectors, and especially in the Baculovirus system, which is advantageously the baculovirus AcNPV (Autographa californica nuclear polyhedrosis virus).

The p80-encoding nucleotide sequence is introduced into an appropriate expression vector according to known techniques for constructing these vectors, especially those described in Patent Application EP-A-0,208,672.

Of course, the abovementioned nucleotide sequence includes all equivalent sequences, that is to say, which possess the essential properties of the sequence. By way of example, this would be the case for a sequence encoding an identical amino acid sequence, but which would use other specific codons by degeneration of the code. This would also be the case for a sequence encoding an amino acid sequence which is no longer identical but similar, taking into account the similarities between amino acids.

Equivalent sequence is also understood to mean a p80-encoding sequence derived from another BVD strain and maintaining recognition by anti-p80 antibodies.

The recombinant antigen is itself obtained from cultures of eukaryotic host cells which have been transfected with the p80-expressing vector, and preferably consists of extracts of these cells. The eukaryotic hosts may be animal or yeast, especially Saccharomyces cerevisiae, cell cultures. The transfer vectors for yeasts advantageously contain markers enabling useful recombinants to be selected for example by resistance to antibiotics or by other known means of selection (Broach J. et al., Meth. Enz. (1983) 101: 307). For the promoters, see also Hess et al., J. Adv. Enz. Reg. (1968) 7/149, and Holland et al., Biochemistry (1968) 17: 4900 or Itzeman et al., J. Biol. Chem. (1980) 255: 2073.

The animal cells are, preferably, known mammalian cell lines such as HeLa, CHO or BEK, insect cells, for example Spodoptera frugiperda (deposit ATCC CRL 1711, Sf9) (especially for the Baculovirus system) and, in general, lines whose use for the expression of substances to be administered to animals has been recognised by the health authorities, will be preferred. Viral promoters such as those of the SV40 virus (Fiers et al., Nature, (1978) 273:113) and of the CMV virus or human cytomegalovirus (McGregor and Caskey, Nucleic Acids Res. 17:2365, 1989), or alternatively, that of the polyhedrin gene of the Baculovirus AcNPV or Autographa californica nuclear polyhedrosis virus (Hooft van Iddekinge et al., 1983, Virology 131: 561–565), will be used as promoter in these cellular constructs.

The recombinant antigen is preferably immobilised on a solid support (for example microtiter plates), especially via an anti-p80 monoclonal antibody which is used as captor. Dilutions of bovine sera are placed in contact with the immobilised or nonimmobilised antigen and the anti-BVD antibodies are either directly revealed by a bovine anti-IgG antiserum coupled for example to peroxidase or biotin (indirect ELISA), or revealed by competition ELISA with a second anti-p80 monoclonal antibody coupled for example to peroxidase or biotin. In fact this detection may be carried out on any bovine blood fraction, especially serum and plasma.

Preferably, the viral particles in crude or white blood cell-enriched whole blood are revealed by mere centrifugation, especially for 30 minutes at 2500 g.

In order to ensure complete detection of the presence of viral particles of all the BVD types, a mixture of three p80-specific monoclonal antibodies is used as captor instead of a single monoclonal antibody.

A sandwich type ELISA is preferably carried out using, as captor, the mixture of three viral p80-specific monoclonal antibodies, and as stain, the serum directed against the recombinant p80 protein. The serum is derived in particular from the immunisation of animals, in particular rabbits or goats, by repeated inoculations of recombinant p80 which may be produced both in prokaryotic and eukaryotic cells.

Samples corresponding to a viral titre of less than for example $10^3$ pfu/ml (pfu=plaque-forming units) may thus be detected as positive. In effect, the invention makes it possible to detect as positive, samples which, by the normal method of immunofluorescence on infected cells, may require three successive passages of the virus and the choice of appropriate host cells, which makes it necessary to propagate the virus on several cell types.

Since the p80 protein does not contain neutralisation epitopes, this method advantageously enables a distinction to be made between animals infected naturally and animals vaccinated with a recombinant vaccine based on the structural proteins of the virus.

The subject of the invention is also the nucleotide sequence with the reference SEQ ID No: 1 which corresponds to the BVD Osloss sequence encoding the nonstructural protein p80, or an equivalent sequence according to the definition given above, as well as any new nucleotide sequence containing it and comprising means permitting its expression or associated with such means.

The subject of the invention is also the recombinant p80 protein corresponding to the translation of this sequence, especially in a eukaryotic host, in the abovementioned expression systems, and any recombinant antigen containing this sequence, especially consisting of extracts of host cells, in particular eukaryotic cells, as stated above.

I—LOCATION AND SEQUENCING OF THE SEQUENCE ENCODING p80

Figure 1:
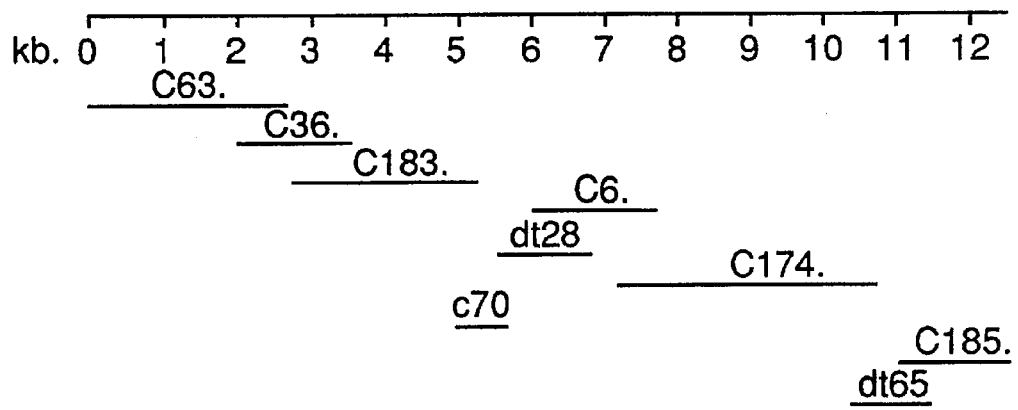
FIG. 1 shows the position of the cDNA clones spanning the entire genome of the BVD virus (Osloss strain).

1. The cDNA C174 was cloned (pcP 174 clone from the cDNA library described in European Patent Application EP-A-0,208,672) (FIG. 1) into the plasmid pSP65, downstream of the RNA polymerase promoter of the bacteriophage SP6, between the EcoRI and BamHI sites (vector described by Melton D. A. et al., 1984, Nucleic Acids Res. 12:7035–7056).

Figure 2:
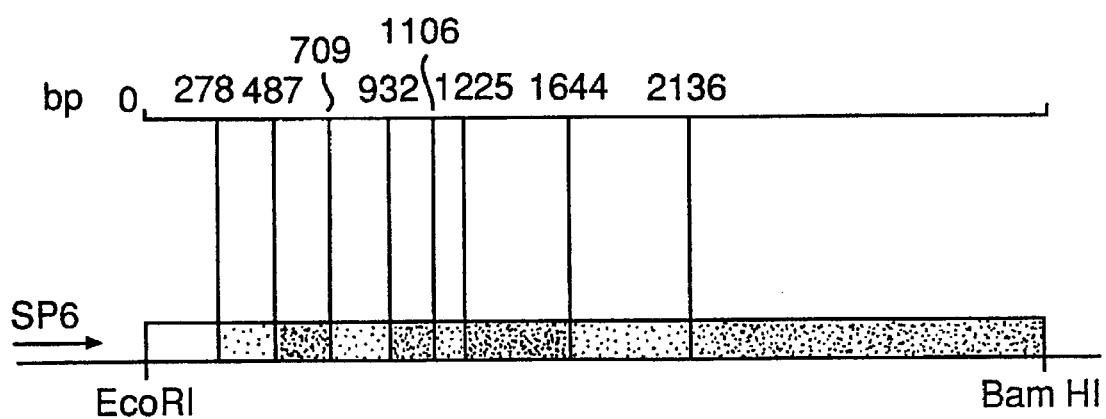
FIG. 2 shows the analysis in vitro of the region of the BVD Osloss genome corresponding to the cDNA clone 174. The numbers therein indicate the size (base pairs=bp) of the various fragments obtained by digestion of the 174 insert by each of the restriction enzymes used.

2. After digestion with various restriction enzymes whose position of successive sites is indicated in FIG. 2, each fragment obtained was transcribed in vitro and then translated in an acellular system (lysate of rabbit reticulocytes). The translational products of increasing molecular weight were immuno-precipitated with anti-p80 monoclonal antibodies; this made it possible to locate an immunoreactive region 80 amino acids in length, which is located in FIG. 3 and whose sequence is given in the list of sequences under the reference SEQ ID No: 2.

Figure 4:
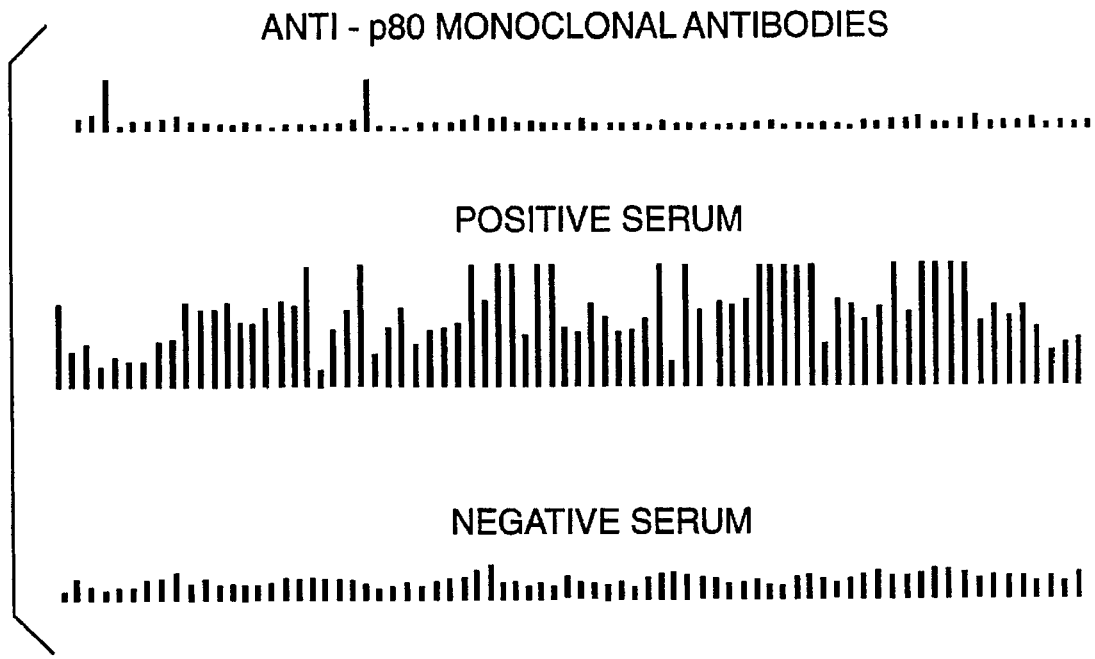
FIG. 4 shows the screening of epitopes in the immunoreactive region, which is 80 amino acids in length, situated within the p80 protein.

3. The presence of recognised epitopes in this region of 80 amino acids was confirmed by epitope scanning, that is to say that 75 peptide hexamers spanning this region were synthesised on a solid support and tested by ELISA in the presence of anti-p80 monoclonal antibodies and antibody-positive or negative bovine sera. The result is illustrated in FIG. 4.

4. Following the location of the anti-p80 epitopes, the sequence encoding the p80 protein was reconstituted so as to resemble the natural protein as much as possible. The presence of one potential cleavage site (KVR: lysine-valine-arginine) corresponding to the end of p80 was determined by analysis of the genomic sequence of the BVD/Osloss virus and by comparison with that of known Flaviviridae; the theoretical molecular weight of the protein between these two sites is 80430 daltons. The first of the two triplets occurs exactly at the same position in the genome of the BVD/NADL virus, and the entire BVD/Osloss genome contains only 5 KVR triplets all situated in the portion encoding the nonstructural proteins of the virus (the NADL genome contains only three of them).

Figure 3:
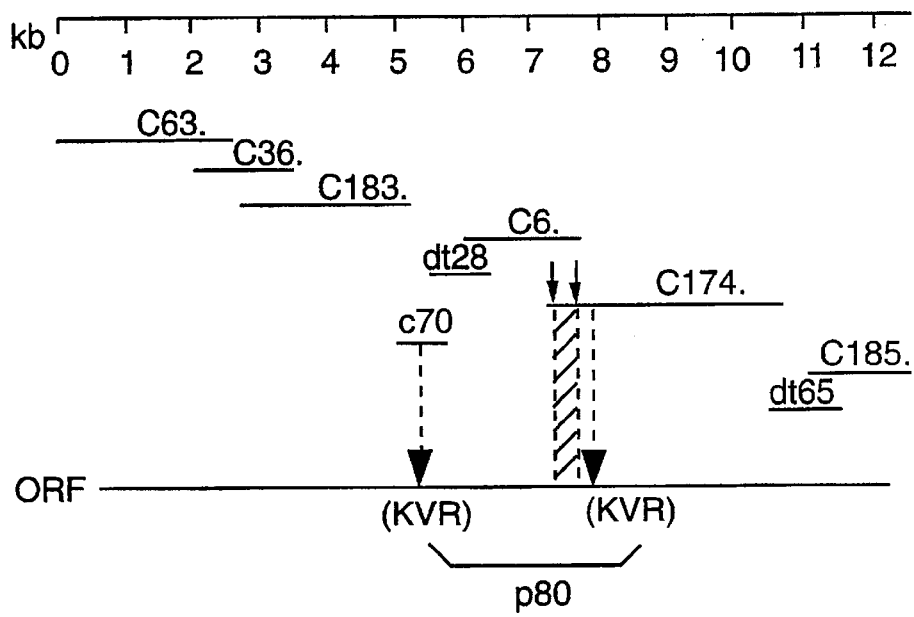
FIG. 3 shows the location, on the BVD Osloss genome, of the immunoreactive region of 80 amino acids and limits of the p80 protein.

The p80 fragment of 2200 bp (base pairs) corresponding to the p80-encoding sequence was amplified by PCR (polymerase chain reaction) and cloned; its location is illustrated in FIG. 3; its nucleotide sequence has the reference SEQ ID No:1.

II—EXPRESSION OF THE RECOMBINANT ANTIGEN

Figure 5:
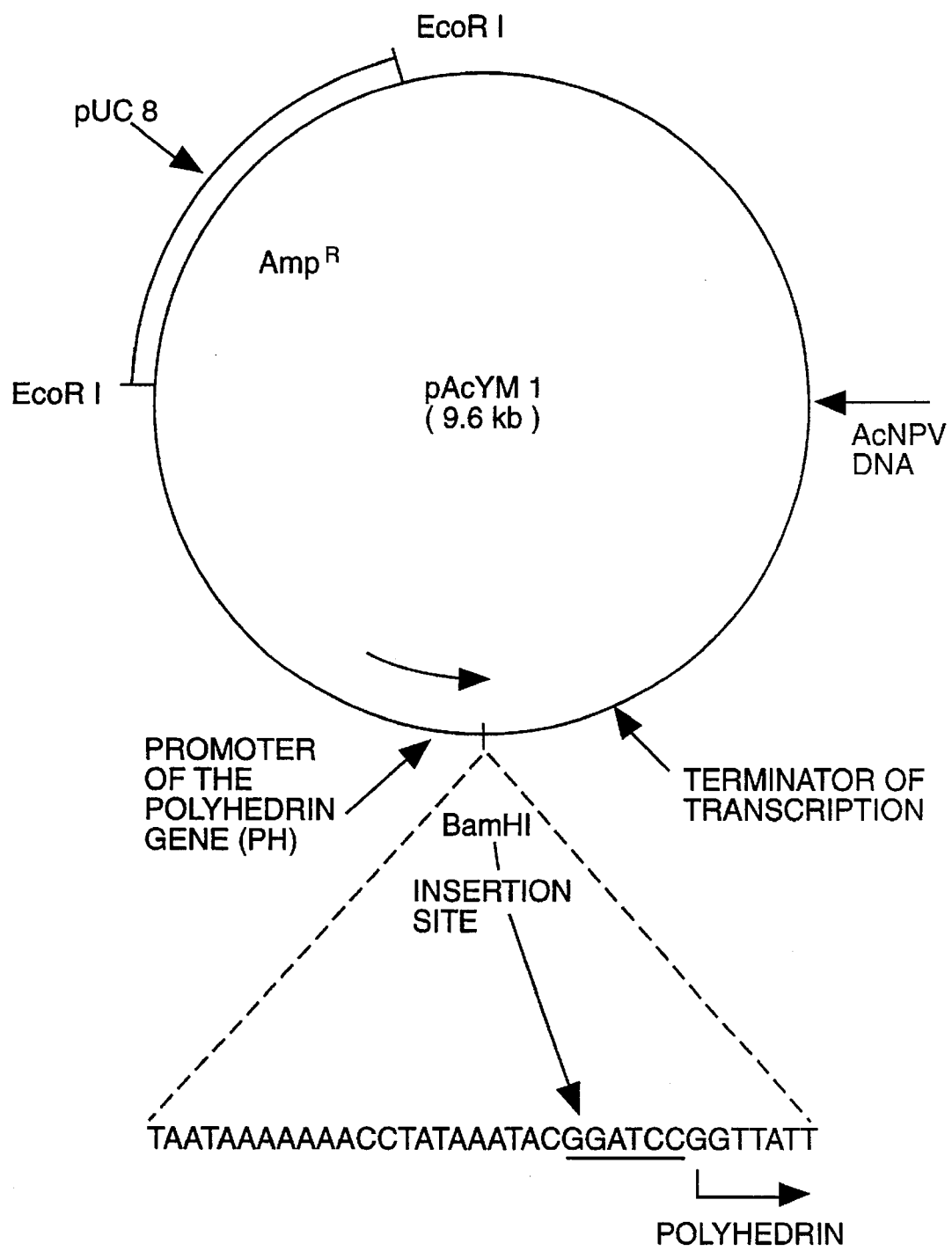
FIG. 5 shows the map of the transfer vector pAcYM1 described by Matsura et al. in J. Gen. Virol. (1987), 68: 1233 to 1250.

The integration of the p80 fragment into the genome of the Baculovirus Autographa californica nuclear polyhedrosis virus (AcNPV) was carried out via the transfer vector pAcYM1 described by Matsura et al. (J. Gen. Virol. 68: 1233–1250, 1987; restriction map in FIG. 5) downstream of the promoter of the AcNPV polyhedrin gene. This vector contains the polyadenylation site of the polyhedrin gene as well as the gene for resistance to ampicillin and the replication origin of the plasmid pUC8 (J. Messing, 1983, Meth. Enzymol. 101:20).

To this effect, the amplified fragment of the sequence SEQ ID No: 1 is digested with the restriction enzymes NcoI and BamHI and then treated with DNA polymerase (Klenow fragment) so as to make the 5' and 3' ends of the fragment blunt. It is then cloned into the BamHI-digested vector pAcYM1 and treated with DNA polymerase (Klenow fragment) so as to make the ends blunt. The recombinant plasmid pAcYM1-p80 is obtained, p80 being expressed under the control of the promoter of the polyhedrin gene.

The plasmid obtained is used to cotransfect the insect cells Sf9 together with the DNA purified from the wild type AcNPV. A recombinant virus AcNPV-p80 was purified by plating the cotransfection supernatant and isolating the viral plaques by covering with agarose.

III—ELISA TEST FOR DETECTING ANTI-p80 ANTIBODIES

Principle:

The test is based on the detection of anti-p80 antibodies, in other words, antibodies directed against a nonstructural protein of 80,000 daltons associated with infection by the BVD virus.

A recombinant antigen comprising the p80 protein derived from the Osloss virus is bound to a solid support via a monoclonal antibody which is used as captor. The bovine blood or serum sample is placed in contact with the bound antigen and is then either directly revealed by a coupled bovine anti-IgG antiserum, or placed in competition with a second coupled anti-p80 monoclonal antibody.

Materials, reagents and samples:

1. Materials and buffers:

96-well ELISA plates (NUNC-MAXISORP);

carbonate buffer, pH 9.6: 15 mM $Na_2CO_3$, 35 mM $NaHCO_3$, 3 mM $NaN_3$;

wash buffers: (1) PBS, (2) PBS, 0.1% Tween 20;

dilution buffer: PBS, 0.1% Tween 20, 10% horse serum (assessed to be free of BVD virus);

saturation buffer: PBS, 10% horse serum (assessed to be free of BVD virus);

chromogen and appropriate buffer.

2. Reagents:

1 anti-p80 monoclonal antibody used as captor of the antigen p80 (dilute ascites liquid);

recombinant p80 antigen;

a) competition ELISA: 1 anti-p80 monoclonal antibody diluted and coupled to peroxidase or biotin;

b) indirect ELISA: bovine anti-IgG serum (rabbit or goat) coupled to peroxidase or biotin.

3. Preparation of the samples:

serum samples: collection of blood in tubes without anticoaqulant; coagulation, minimum 4 hours at room temperature; centrifugation 2500 g, 30 minutes; collect the supernatant=serum;

the test may be carried out on any blood fraction, especially plasma or even whole blood collected in tubes with anticoagulant.

Method:

1. Binding of the captor:

The dilute anti-p80 monoclonal antibody is distributed in an amount of 100 µl per well:

contact overnight at 4° C.;

3 washes with buffer (1).

2. Saturation (optional):

150 µl/well of saturation buffer:

1 hour at 37° C.

3. Binding of the antigen:

recombinant p80 antigen (100 µl/well)

contact overnight at 4° C.

4. Contact with the samples:

100 µl/well; sera diluted 10×:

contact 2 hours at 37° C., 3 washes with buffer (1).

5. Contact with the staining antibody:

a) Competition ELISA: contact with dilute and coupled monoclonal antibody:

1 h 30 min at 37° C.;

3 washes with buffer (2);

3 washes with water.

b) Indirect ELISA: contact with dilute and coupled bovine anti-IgG serum;

1 h 30 min at 37° C.;

3 washes with buffer (2);

3 washes with water.

6. Staining with the chromogen:

The procedure varies according to the chromogen and is detailed by its supplier.

IV—ELISA TEST FOR DETECTING VIRAL PARTICLES

Principle:

The test is based on the detection of the p80 protein, a nonstructural protein of the BVD virus which is present in a large amount in the blood of infected animals. A mixture of three monoclonal antibodies specific for this p80 protein is used as captor and bound to the solid support (microtiter plates). Whole blood or the fraction of blood enriched with white blood cells or "buffy coat" is placed in contact with the bound captor mixture. A serum (rabbit or goat), directed against the recombinant p80 protein, is used as staining antibody either directly coupled (to peroxidase or biotin), or itself stained with a second antibody (rabbit or goat anti-IgG) coupled to peroxidase or biotin.

The presence of viral antigen in the tested samples is indicated by the increase in the initial optical density in the presence of chromogen.

Materials, reagents and samples:
1. Materials and buffers:
   96-well ELISA plates: NUNC-MAXISORP;
   carbonate buffer, pH 9.6: 15 mM $Na_2CO_3$, 35 mM $NaHCO_3$, 3 mM $NaN_3$;
   wash buffer: PBS, 0.1% Tween 20;
   saturation/dilution buffer: PBS, 0.1% Tween 20, 10% horse serum (assessed to be free of BVD virus);
   chromogen and appropriate buffer.
2. Reagents:
   mixture of 3 anti-p80 monoclonal antibodies, dilute ascites liquids;
   serum (rabbit or goat) directed against the recombinant p80 protein, either directly coupled (to peroxidase or biotin), or itself stained with a second antibody (rabbit or goat anti-IgG) coupled to peroxidase or biotin.
3. Preparation of the samples:
   Collection of blood in heparinised tubes; the samples are tested either as they are, or after enrichment with white blood cells according to the following procedure: centrifugation at 2500 g; 30 minutes; after centrifugation, removing the upper layer consisting of plasma by pipetting, and collecting the buffy coat, a whitish zone situated between the plasma and the red blood cells.

Method:
1. Binding of the captor:
   Mixture of monoclonal antibodies diluted and distributed in an amount of 100 µl per well;
   contact overnight at 4° C.;
   3 washes in PBS/Tween.
2. Saturation:
   150 µl well of saturation buffer containing 10% of horse serum;
   1 hour at 37° C.
3. Contact with the samples:
   100 µl of whole blood or buffy coat per well;
   contact 2 hours at 37° C.;
   3 washes in PBS/Tween.
4. Contact with the staining antibody:
   Dilute anti-p80 serum, coupled or uncoupled (peroxidase or biotin):
   contact 1 h at 37° C. (100 µl/well);
   3 washes in PBS/Tween;
   3 washes with water;
   If uncoupled serum is used, repeat contact with coupled antiserum (1 hour at 37° C.).
5. Staining with the chromogen:
   The procedure varies according to the chromogen chosen and is detailed by its supplier.

LIST OF SEQUENCES.

SEQ ID No: 1
TYPE OF SEQUENCE: nucleotide sequence
LENGTH OF SEQUENCE: 2236 base pairs
NUMBER OF STRANDS: single
CONFIGURATION: linear
TYPE OF MOLECULE: cDNA for genomic RNA
ORIGIN: BVD Osloss
REGION TRANSLATED: 40–2229
PROPERTIES: encodes the protein p80

```
                                                          Met Gly Leu     3
TCT AGA AAT TTT GTT TAA CTT TAA GAA GGA GAT ATA CCC ATG GGA CTG    48
 XbaI                                               NcoI

Glu Thr Gly Trp Ala Tyr Thr His Gln Gly Gly Ile Ser Ser Val Asp    19
GAA ACC GGA TGG GCC TAC ACA CAC CAA GGC GGC ATA AGC TCA GTA GAC    96

His Val Thr Ala Gly Lys Asp Leu Leu Val Cys Asp Ser Met Gly Arg    35
CAT GTG ACC GCA GGC AAA GAC CTA CTG GTT TGT GAT AGT ATG GGT AGG   144

Thr Arg Val Val Cys Gln Ser Asn Asn Lys Leu Thr Asp Glu Thr Glu    51
ACA AGA GTG GTT TGC CAA AGT AAC AAC AAG TTA ACT GAT GAG ACA GAA   192

Tyr Gly Val Lys Thr Asp Ser Gly Cys Pro Asp Gly Ala Arg Cys Tyr    67
TAT GGT GTC AAG ACG GAC TCC GGA TGT CCA GAT GGT GCC AGG TGC TAC   240

Val Leu Asn Pro Glu Ala Val Asn Ile Ser Gly Ser Lys Gly Ala Ala    83
GTA TTA AAT CCA GAG GCA GTA AAT ATA TCA GGG TCC AAG GGA GCT GCT   288

Val His Leu Gln Lys Thr Gly Gly Glu Phe Thr Cys Val Thr Ala Ser    99
GTA CAC CTC CAA AAA ACA GGT GGG GAA TTC ACA TGT GTT ACT GCA TCG   336

Gly Thr Pro Ala Phe Phe Asp Leu Lys Asn Leu Lys Gly Trp Ser Gly   115
GGA ACT CCA GCC TTC TTT GAC CTG AAA AAT TTG AAG GGA TGG TCA GGT   384

Leu Pro Ile Phe Glu Ala Ser Ser Gly Arg Val Val Gly Arg Val Lys   131
CTA CCC ATA TTT GAG GCT TCT AGT GGC AGG GTG GTC GGC AGA GTT AAA   432
```

-continued
LIST OF SEQUENCES.

| | | | | | | | | | | | | | | | |
|---|---|---|---|---|---|---|---|---|---|---|---|---|---|---|---|
| Val | Gly | Lys | Asn | Glu | Glu | Ser | Lys | Pro | Thr | Lys | Leu | Met | Ser | Gly | Ile | 147 |
| GTA | GGA | AAG | AAT | GAG | GAA | TCC | AAG | CCC | ACA | AAA | TTA | ATG | AGT | GGT | ATC | 480 |
| Gln | Thr | Val | Ser | Lys | Ser | Thr | Ala | Asp | Leu | Thr | Glu | Met | Val | Lys | Lys | 163 |
| CAA | ACC | GTC | TCA | AAA | AGC | ACA | GCC | GAT | TTA | ACA | GAG | ATG | GTC | AAG | AAG | 528 |
| Ile | Thr | Ser | Met | Asn | Arg | Gly | Asp | Phe | Lys | Gln | Ile | Thr | Leu | Ala | Thr | 179 |
| ATA | ACC | AGC | ATG | AAC | AGG | GGA | GAC | TTT | AAG | CAG | ATA | ACC | CTT | GCA | ACA | 576 |
| Gly | Ala | Gly | Lys | Thr | Thr | Glu | Leu | Pro | Lys | Ala | Val | Ile | Glu | Glu | Ile | 195 |
| GGG | GCA | GGA | AAA | ACT | ACA | GAA | CTC | CCA | AAG | GCA | GTG | ATA | GAG | GAG | ATA | 624 |
| Gly | Arg | His | Lys | Arg | Val | Leu | Val | Leu | Ile | Pro | Leu | Arg | Ala | Ala | Ala | 211 |
| GGA | AGA | CAC | AAG | CGG | GTG | CTA | GTG | CTT | ATA | CCA | TTG | AGA | GCA | GCA | GCT | 672 |
| Glu | Ser | Val | Tyr | Gln | Tyr | Met | Arg | Leu | Lys | His | Pro | Ser | Ile | Ser | Phe | 227 |
| GAG | TCA | GTC | TAT | CAA | TAC | ATG | AGA | TTG | AAA | CAT | CCC | AGT | ATC | TCC | TTC | 720 |
| Asn | Leu | Arg | Ile | Gly | Asp | Met | Lys | Glu | Gly | Asp | Met | Ala | Thr | Gly | Ile | 243 |
| AAC | TTA | AGA | ATA | GGG | GAC | ATG | AAA | GAA | GGG | GAC | ATG | GCA | ACT | GGG | ATC | 768 |
| Thr | Tyr | Ala | Ser | Tyr | Gly | Tyr | Phe | Cys | Gln | Met | Pro | Gln | Pro | Lys | Leu | 259 |
| ACC | TAC | GCC | TCA | TAT | GGA | TAT | TTT | TGC | CAA | ATG | CCG | CAG | CCG | AAG | CTC | 816 |
| Arg | Ala | Ala | Met | Val | Glu | Tyr | Ser | Tyr | Ile | Phe | Leu | Asp | Glu | Tyr | His | 275 |
| AGG | GCC | GCA | ATG | GTA | GAG | TAT | TCA | TAC | ATA | TTT | CTG | GAT | GAG | TAT | CAC | 864 |
| Cys | Ala | Thr | Pro | Glu | Gln | Leu | Ala | Val | Ile | Gly | Lys | Ile | His | Arg | Phe | 291 |
| TGT | GCT | ACT | CCT | GAG | CAG | TTG | GCT | GTC | ATA | GGA | AAA | ATT | CAC | AGA | TTT | 912 |
| Ser | Glu | Ser | Ile | Arg | Val | Val | Ala | Met | Thr | Ala | Thr | Pro | Ala | Gly | Ser | 307 |
| TCT | GAA | AGC | ATA | AGG | GTG | GTT | GCT | ATG | ACC | GCC | ACC | CCA | GCA | GGG | TCA | 960 |
| Val | Thr | Thr | Thr | Gly | Gln | Lys | His | Pro | Ile | Glu | Glu | Phe | Ile | Ala | Pro | 323 |
| GTA | ACT | ACA | ACA | GGG | CAA | AAA | CAC | CCA | ATA | GAA | GAA | TTC | ATA | GCT | CCT | 1008 |
| Glu | Val | Met | Lys | Gly | Glu | Asp | Leu | Gly | Ser | Gln | Phe | Leu | Asp | Ile | Ala | 339 |
| GAG | GTG | ATG | AAA | GGG | GAA | GAC | CTT | GGA | AGC | CAG | TTC | CTT | GAC | ATA | GCG | 1056 |
| Gly | Leu | Lys | Ile | Pro | Val | Glu | Glu | Met | Lys | Gly | Asn | Met | Leu | Val | Phe | 355 |
| GGG | CTA | AAA | ATC | CCG | GTT | GAG | GAG | ATG | AAG | GGT | AAC | ATG | CTG | GTC | TTC | 1104 |
| Val | Pro | Thr | Arg | Asn | Met | Ala | Val | Asp | Val | Ala | Lys | Lys | Leu | Lys | Ala | 371 |
| GTA | CCC | ACA | AGA | AAC | ATG | GCA | GTT | GAT | GTA | GCC | AAG | AAA | CTA | AAA | GCC | 1152 |
| Lys | Gly | Tyr | Asn | Ser | Gly | Tyr | Tyr | Tyr | Ser | Gly | Glu | Asp | Pro | Ala | Asn | 387 |
| AAG | GGC | TAC | AAC | TCA | GGG | TAT | TAC | TAC | AGT | GGG | GAA | GAC | CCG | GCT | AAC | 1200 |
| Leu | Arg | Val | Val | Thr | Ser | Gln | Ser | Pro | Tyr | Val | Val | Val | Ala | Thr | Asn | 403 |
| TTG | AGG | GTG | GTA | ACA | TCA | CAG | TCC | CCA | TAC | GTC | GTA | GTA | GCC | ACC | AAT | 1248 |
| Ala | Ile | Glu | Ser | Gly | Val | Thr | Leu | Pro | Asp | Leu | Asp | Thr | Val | Val | Asp | 419 |
| GCC | ATT | GAG | TCA | GGG | GTA | ACG | CTG | CCA | GAT | TTA | GAT | ACA | GTT | GTT | GAC | 1296 |
| Thr | Gly | Leu | Lys | Cys | Glu | Lys | Arg | Val | Arg | Val | Ser | Ser | Lys | Ile | Pro | 435 |
| ACA | GGT | CTG | AAG | TGT | GAA | AAG | AGG | GTG | AGG | GTG | TCA | TCA | AAA | ATA | CCT | 1344 |
| Phe | Ile | Val | Thr | Gly | Leu | Lys | Arg | Met | Ala | Val | Thr | Val | Gly | Glu | Gln | 451 |
| TTC | ATA | GTA | ACA | GGC | CTT | AAA | AGA | ATG | GCT | GTC | ACT | GTG | GGC | GAA | CAG | 1392 |
| Ala | Gln | Arg | Arg | Gly | Arg | Val | Gly | Arg | Val | Lys | Pro | Gly | Arg | Tyr | Tyr | 467 |
| GCT | CAG | CGA | AGA | GGC | AGG | GTA | GGT | AGA | GTG | AAG | CCC | GGT | AGG | TAC | TAT | 1440 |
| Arg | Ser | Gln | Glu | Thr | Ala | Thr | Gly | Ser | Lys | Asp | Tyr | His | Tyr | Asp | Leu | 483 |
| AGA | AGC | CAG | GAA | ACA | GCG | ACC | GGG | TCA | AAG | GAC | TAC | CAC | TAT | GAC | CTG | 1488 |
| Leu | Gln | Ala | His | Arg | Tyr | Gly | Ile | Glu | Asp | Gly | Ile | Asn | Val | Thr | Lys | 499 |
| TTA | CAG | GCA | CAC | AGG | TAT | GGG | ATA | GAA | GAT | GGA | ATC | AAC | GTG | ACA | AAG | 1536 |
| Ser | Phe | Arg | Glu | Met | Asn | Tyr | Asp | Trp | Ser | Leu | Tyr | Glu | Glu | Asp | Ser | 515 |
| TCC | TTT | AGG | GAA | ATG | AAT | TAC | GAT | TGG | AGC | CTG | TAC | GAG | GAG | GAC | AGC | 1584 |
| Leu | Leu | Ile | Thr | Gln | Leu | Glu | Ile | Leu | Asn | Asn | Leu | Leu | Ile | Ser | Glu | 531 |
| TTG | CTG | ATA | ACG | CAG | CTG | GAG | ATA | CTG | AAC | AAT | CTA | CTC | ATC | TCT | GAA | 1632 |
| Asp | Leu | Pro | Ala | Ala | Val | Lys | Asn | Ile | Met | Ala | Arg | Thr | Asp | His | Pro | 547 |
| GAC | CTA | CCA | GCA | GCA | GTA | AAA | AAC | ATC | ATG | GCA | AGG | ACT | GAT | CAC | CCA | 1680 |
| Glu | Pro | Ile | Gln | Leu | Ala | Tyr | Asn | Ser | Tyr | Glu | Val | Gln | Val | Pro | Val | 563 |
| GAA | CCA | ATC | CAG | CTT | GCA | TAC | AAC | AGT | TAT | GAG | GTC | CAG | GTC | CCT | GTA | 1728 |

-continued
LIST OF SEQUENCES.

```
Leu Phe Pro Lys Ile Arg Asn Gly Glu Val Thr Asp Thr Tyr Glu Asn  579
CTG TTT CCA AAA ATA AGG AAT GGG GAG GTT ACA GAT ACT TAC GAG AAC 1776

Tyr Ser Phe Leu Asn Ala Arg Lys Leu Gly Glu Asp Val Pro Val Tyr  595
TAC TCA TTC CTA AAT GCA AGA AAA CTA GGG GAA GAT GTA CCT GTG TAC 1824

Ile Tyr Ala Thr Glu Asp Glu Asp Leu Ala Val Asp Leu Leu Gly Leu  611
ATT TAT GCC ACC GAA GAT GAA GAC CTG GCA GTA GAC CTT CTA GGC TTG 1872

Asp Trp Pro Asp Pro Gly Asn Gln Gln Val Val Glu Thr Gly Lys Ala  627
GAC TGG CCC GAC CCA GGG AAC CAG CAA GTA GTG GAG ACT GGG AAA GCA 1920

Leu Lys Gln Val Val Gly Leu Ser Ser Ala Glu Asn Ala Leu Leu Ile  643
CTG AAG CAA GTA GTA GGA CTG TCC TCT GCT GAG AAT GCC CTG CTC ATA 1968

Ala Leu Phe Gly Tyr Val Gly Tyr Gln Ala Leu Ser Lys Arg His Val  659
GCC CTG TTT GGG TAT GTA GGA TAT CAA GCT TTG TCA AAA AGA CAC GTC 2016

Pro Met Ile Thr Asp Ile Tyr Thr Ile Glu Asp Gln Arg Leu Glu Asp  675
CCA ATG ATC ACA GAC ATA TAC ACC ATA GAA GAT CAA AGA CTA GAG GAC 2064

Thr Thr His Leu Gln Tyr Ala Pro Asn Ala Ile Arg Thr Glu Gly Lys  691
ACA ACC CAC CTC CAA TAT GCA CCT AAT GCT ATA AGA ACT GAG GGG AAG 2112

Glu Thr Glu Leu Lys Glu Leu Ala Val Gly Asp Met Asp Arg Ile Met  707
GAG ACT GAA CTA AAG GAA TTA GCA GTG GGT GAC ATG GAC AGA ATC ATG 2160

Glu Ser Ile Ser Asp Tyr Ala Ser Gly Gly Leu Thr Phe Ile Arg Ser  723
GAA TCC ATC TCA GAT TAT GCA TCA GGA GGG TTG ACA TTC ATA AGA TCT 2208

STOP
Gln Ala Glu Lys Val Arg  ***                                      729
CAG GCA GAG AAA GTA CGC TAG  CGG ATC C                           2236
                              BamHI
```

SEQ ID No: 2
TYPE OF SEQUENCE: nucleotide sequence
LENGTH OF SEQUENCE: 240 base pairs
NUMBER OF STRANDS: single
CONFIGURATION: linear
TYPE OF MOLECULE: cDNA for genomic RNA
ORIGIN: BVD Osloss
REGION TRANSLATED: 1–240
PROPERTIES: encodes a p80 region of 80 amino
             acids comprising epitopes recognised
             by anti-p80 monoclonal antibodies.

```
Gly Tyr Gln Ala Leu Ser Lys Arg His Val Pro Met Ile Thr Asp Ile   16
GGA TAT CAA GCT TTG TCA AAA AGA CAC GTC CCA ATG ATC ACA GAC ATA   48

Tyr Thr Ile Glu Asp Gln Arg Leu Glu Asp Thr Thr His Leu Gln Tyr   32
TAC ACC ATA GAA GAT CAA AGA CTA GAG GAC ACA ACC CAC CTC CAA TAT   96

Ala Pro Asn Ala Ile Arg Thr Glu Gly Lys Glu Thr Glu Leu Lys Glu   48
GCA CCT AAT GCT ATA AGA ACT GAG GGG AAG GAG ACT GAA CTA AAG GAA  144

Leu Ala Val Gly Asp Met Asp Arg Ile Met Glu Ser Ile Ser Asp Tyr   64
TTA GCA GTG GGT GAC ATG GAC AGA ATC ATG GAA TCC ATC TCA GAT TAT  192

Ala Ser Gly Gly Leu Thr Phe Ile Arg Ser Gln Ala Glu Lys Val Arg   80
GCA TCA GGA GGG TTG ACA TTC ATA AGA TCT CAG GCA GAG AAA GTA AGA  240
```

We claim:

1. Nucleotide sequence consisting of SEQ ID No: 1.
2. Recombinant protein consisting of expression of the ORF of SEQ ID No: 1.
3. Recombinant protein according to claim 2 that is produced in a eukaryotic host.
4. Recombinant protein according to claim 3 that is produced in *Spodoptera frugiperda* insect cells transfected with a Baculovirus vector.
5. Recombinant protein according to claim 4 wherein the Baculovirus vector in Baculovirus AcNPV.

* * * * *